US009545478B2

(12) United States Patent
Abal

(10) Patent No.: US 9,545,478 B2
(45) Date of Patent: *Jan. 17, 2017

(54) INTRAVENOUS INFUSION TUBING FITMENT AND SET

(71) Applicant: CareFusion 303, Inc., San Diego, CA (US)

(72) Inventor: Daniel Abal, San Diego, CA (US)

(73) Assignee: CareFusion Corporation, San Diego, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 14/242,461

(22) Filed: Apr. 1, 2014

(65) Prior Publication Data

US 2014/0213986 A1   Jul. 31, 2014

Related U.S. Application Data

(63) Continuation of application No. 12/987,318, filed on Jan. 10, 2011, now Pat. No. 8,690,860.

(51) Int. Cl.
*A61M 5/168* (2006.01)

(52) U.S. Cl.
CPC ..... *A61M 5/16881* (2013.01); *A61M 5/16804* (2013.01); *A61M 5/16813* (2013.01); *A61M 5/16877* (2013.01); *A61M 2205/60* (2013.01); *Y10T 29/49826* (2015.01)

(58) Field of Classification Search
CPC .................. A61M 5/16881; A61M 5/16804; A61M 5/16813; A61M 5/16877; A61M 2205/60
See application file for complete search history.

(56) References Cited

U.S. PATENT DOCUMENTS

| 4,504,263 | A | * | 3/1985 | Steuer | A61B 5/208 128/DIG. 13 |
| 4,769,012 | A | * | 9/1988 | Quang | A61M 5/16881 137/504 |
| 5,005,604 | A |   | 4/1991 | Aslanian | |

(Continued)

FOREIGN PATENT DOCUMENTS

KR   10 2003 0044181   6/2003

OTHER PUBLICATIONS

ISA/KR,International SearchReport and Written Opinion for International Application No. PCT/US2012/020691, 8 pages, Aug. 14, 2012.

*Primary Examiner* — Bradley Osinski
(74) *Attorney, Agent, or Firm* — Fred C. Hernandez; Mintz Levin Cohn Ferris Glovsky and Popeo, P.C.

(57) ABSTRACT

An intravenous infusion tubing fitment comprises a body, a rotatable knob coupled with the body, and a pressure dome seated within the knob. The body defines; a first inlet configured for coupling with a first segment of tubing; a first outlet into a pressure dome; a second inlet from the pressure dome; and a second outlet configured for coupling with a second segment of tubing. The knob defines an expansion opening within a surface of the knob. The pressure dome is formed of a flexible elastomeric material and defines a fluid flow path between the first outlet and the second inlet. The pressure dome includes a vane configured to variably regulate flow through the fluid flow path in response to rotation of the knob. The pressure dome is configured to expand through the expansion opening in response to fluid pressure in the fluid flow path.

26 Claims, 15 Drawing Sheets

(56) References Cited

U.S. PATENT DOCUMENTS

| | | | |
|---|---|---|---|
| 5,014,750 A | 5/1991 | Winchell et al. | |
| 7,256,888 B2 | 8/2007 | Staehr et al. | |
| 7,361,165 B2 * | 4/2008 | Simon | A61M 5/16804 |
| | | | 604/246 |
| 7,611,503 B2 | 11/2009 | Spohn et al. | |
| 7,785,284 B2 | 8/2010 | Baraldi et al. | |
| 2005/0234428 A1 | 10/2005 | Spohn et al. | |
| 2007/0161970 A1 | 7/2007 | Spohn et al. | |
| 2008/0103445 A1 | 5/2008 | Blaine et al. | |
| 2010/0168711 A1 * | 7/2010 | Bazargan | A61B 5/14546 |
| | | | 604/404 |
| 2010/0243543 A1 | 9/2010 | Sanna | |
| 2012/0179142 A1 | 7/2012 | Abal | |

\* cited by examiner

Section A - A

Section B - B atent a US 9,545,478 B2

INTRAVENOUS INFUSION TUBING FITMENT AND SET

CROSS-REFERENCE TO RELATED APPLICATION

This application is a continuation of U.S. patent application Ser. No. 12/987,318, titled "INTRAVENOUS INFUSION TUBING FITMENT AND SET," filed Jan. 10, 2011, the disclosure of which is hereby incorporated by reference in its entirety herein.

BACKGROUND

Intravenous (IV) infusion sets comprise a variety of components which, when coupled together, facilitate infusing of IV fluid into a body (i.e., a human or animal body). Such IV infusion "sets" may be assembled from a variety of components for a particular use, but are often preassembled and reside in ready-to-use packaging. A set may be assembled or opened, and then connected with a source of IV fluid (i.e., a bag or bottle) on a proximal end and a needle or catheter on the distal end. IV sets may infuse fluid via gravity feed or via pumped pressure feed. When pumped, typically a portion of tubing of the set is inserted into a pump, such as a peristaltic or finger type pump. The pump massages or otherwise interacts with the tubing to pressurize and pump fluid that is flowing through the tubing.

BRIEF DESCRIPTION OF THE DRAWINGS

The accompanying drawings, which are incorporated in and form a part of this application, illustrate embodiments of the subject matter, and together with the description of embodiments, serve to explain the principles of the embodiments of the subject matter. Unless noted, the drawings referred to in this brief description of drawings should be understood as not being drawn to scale.

DESCRIPTION OF EMBODIMENTS

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Overview of Discussion

Herein, an intravenous (IV) infusion set and a tubing fitment thereof are described. The described IV infusion set and tubing fitment can be used with pumped or unpumped (i.e., gravity feed) fluid infusion setups. With an unpumped IV infusion setup, the IV infusion tubing fitment described herein provides at least a mechanism for flow control. With a pumped IV infusion setup, the IV infusion fitment described herein, provides flow control and additionally provides a pressured dome from which fluid pressure can be monitored. Additionally, an IV infusion fitment described herein can also provide an integrated air-in-line sensor fitment for monitoring for air in the IV infusion fluid flow path. Discussion begins with description of an example IV infusion set which includes a tubing fitment of the type described herein. Discussion then continues with description of various features and embodiments of the tubing fitment and features thereof, such as a combined pressure dome and flow control device.

Example Intravenous Infusion Set

Figure 1:
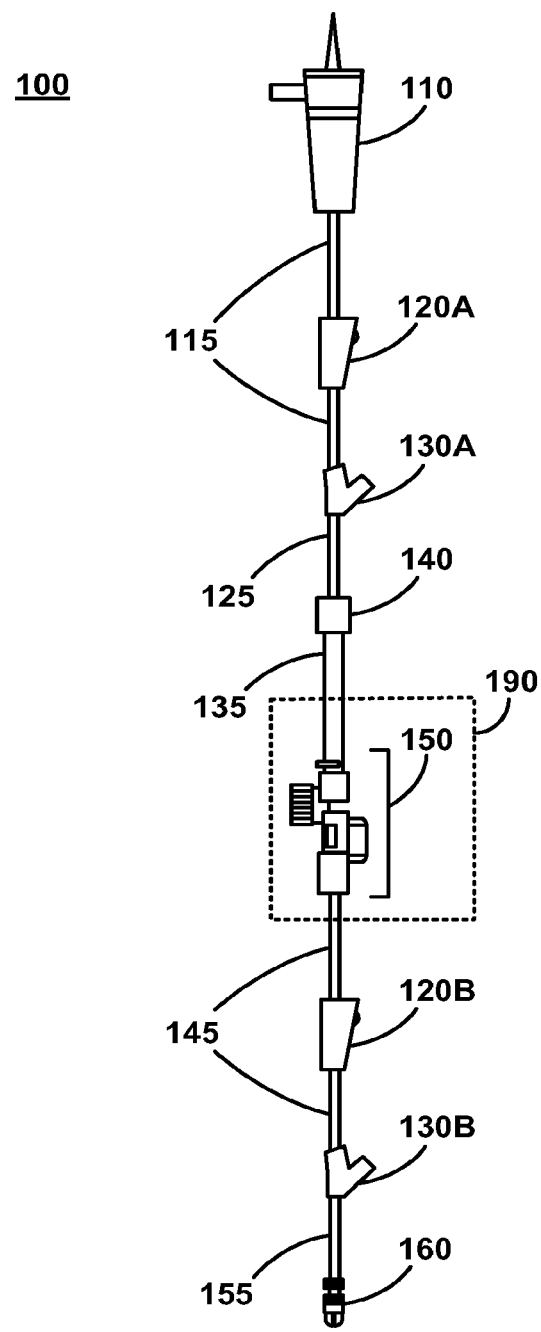
FIG. 1 is a block diagram of an example intravenous (IV) infusion set, according to various embodiments.

FIG. 1 is a block diagram of an example IV infusion set 100, according to various embodiments. As described herein, in one embodiment, an IV infusion set 100 includes at least the portion that is included in dashed box 190, namely: IV infusion tubing fitment 150; tubing 135 which is coupled with the proximal opening of IV infusion tubing fitment 150; and tubing 145 which is coupled with the distal opening of IV infusion tubing fitment 150. FIGS. 2-6, 8, and 9 show detail views of box 190. In other embodiments, an IV infusion set 100 may additionally include one or more of the other components illustrated in FIG. 1 and additionally or alternatively one or more additional components which are not illustrated in FIG. 1. In one embodiment, IV infusion set 100 may be packaged in a sterile state for ready use with a patient (e.g., a human or animal). In one embodiment, IV infusion set 100 may be packaged within a sterilizable packaging for ready sterilization prior to use with a patient.

In one embodiment, an IV infusion set 100 comprises: a universal spike, vent cap, drip chamber 110 (hereafter referred to as "universal spike") for coupling with an intravenous fluid supply such as a bag or bottle; one or more proximal segments of tubing 115, 125; a pumping segment of tubing 135; one or more distal segments of tubing 145, 155; an upper IV infusion tubing fitment 140; a lower IV infusion tubing fitment 150; and a Luer lock adapter 160 (or some other type of adapter) for adaptively coupling IV infusion set 100 with a needle or catheter. In some embodiments, IV infusion set 100 may additionally include: one or more injection ports 130A, 130B; and/or one or more clamps such as roller clamps 120A, 120B for compressing tubing to clamp off the flow of fluid at the various points in the fluid flow path of IV infusion set 100 where the clamps are disposed.

As depicted in FIG. 1, IV infusion set 100 includes universal spike 110 disposed on the proximal end of IV infusion set 100. A first segment of tubing 115 (polyvinyl-chloride (PVC) tubing or some other type of biocompatible tubing) has a proximal end coupled with a distal end of universal spike 110, and has a distal end coupled with a proximal end of Y-injection port 130A. Segment of tubing 115 runs through clamp 120A. Segment of tubing 125 (PVC tubing or some other type of biocompatible tubing) has a proximal end coupled with a distal end of Y-injection port 130A and a distal end coupled with a proximal end of upper intravenous infusion tubing fitment 140. Pumping segment of tubing 135 has a proximal end coupled with a distal opening of upper intravenous infusion tubing fitment 140, and a distal end coupled with a proximal opening of lower intravenous infusion tubing fitment 150. In practice, pumping segment of tubing 135 is typically silicone tubing or other biocompatible tubing with more resilient properties than PVC tubing. A segment of tubing 145 (PVC tubing or some other type of biocompatible tubing) has a proximal end coupled with a distal opening of lower intravenous infusion tubing fitment 150, and has a distal end coupled with a proximal end of Y-injection port 130B. Segment of tubing 145 runs through clamp 120B. A segment of tubing 155 (PVC tubing or some other type of biocompatible tubing) has a proximal end coupled with a distal end of Y-injection port 130B and a distal end coupled with a proximal end of Luer lock adapter 160.

Example Intravenous Tubing Fitment

Figure 2:
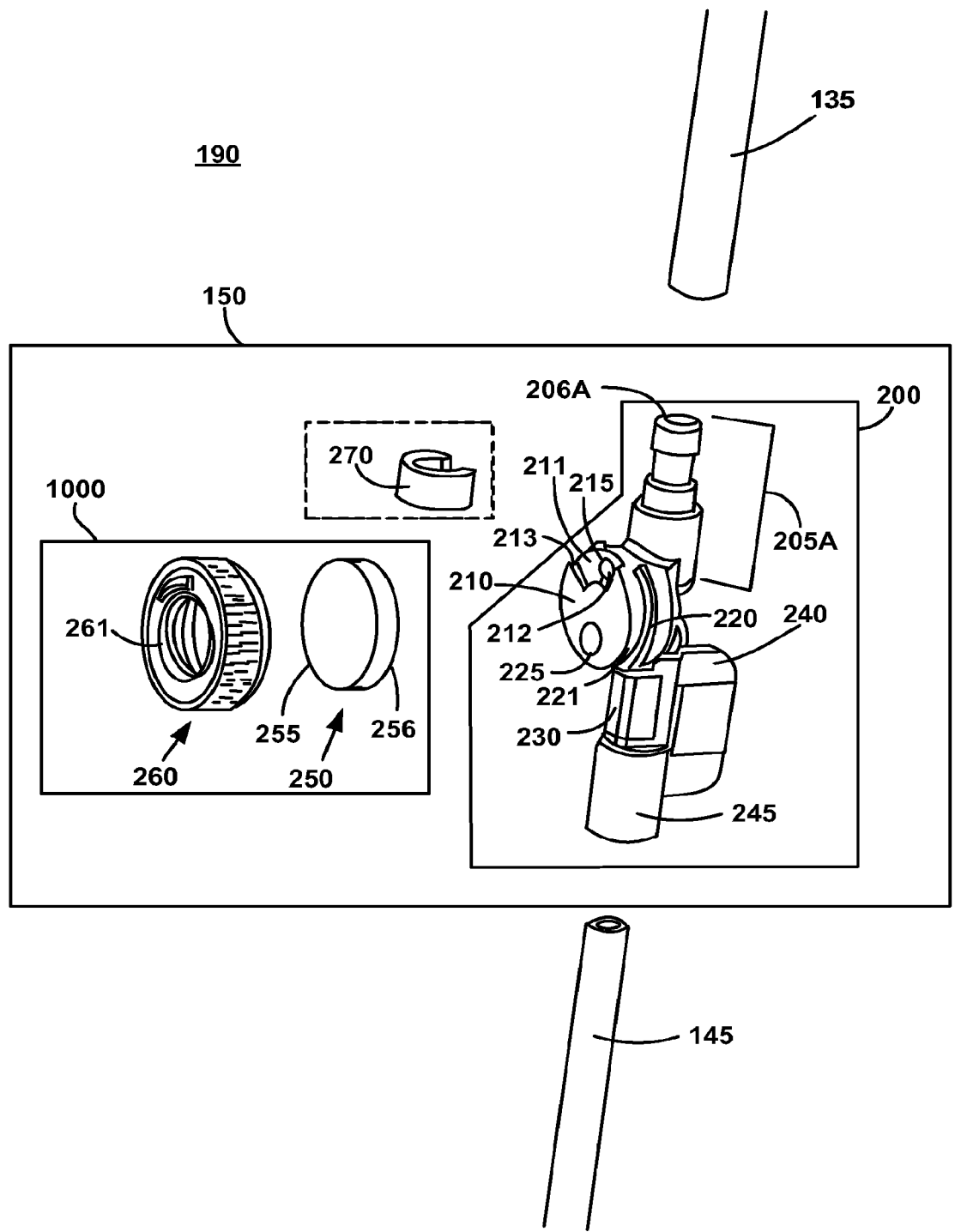
FIG. 2 is an exploded front right detail view of an example IV infusion tubing fitment and components of an IV infusion set, in accordance with an embodiment.

FIG. 2 is an exploded front right detail view of an example IV infusion tubing fitment 150 and tubing components 135, 145 of an IV infusion set 100, in accordance with an embodiment. In detail 190 of FIG. 2, various components and features of IV infusion tubing fitment 150 are visible, including: a body 200; a combined pressure dome and flow control device 1000; and a clamping mechanism 270. In some embodiments, as will be described herein, clamping mechanism 270 is not utilized, or is optional.

Figure 9:
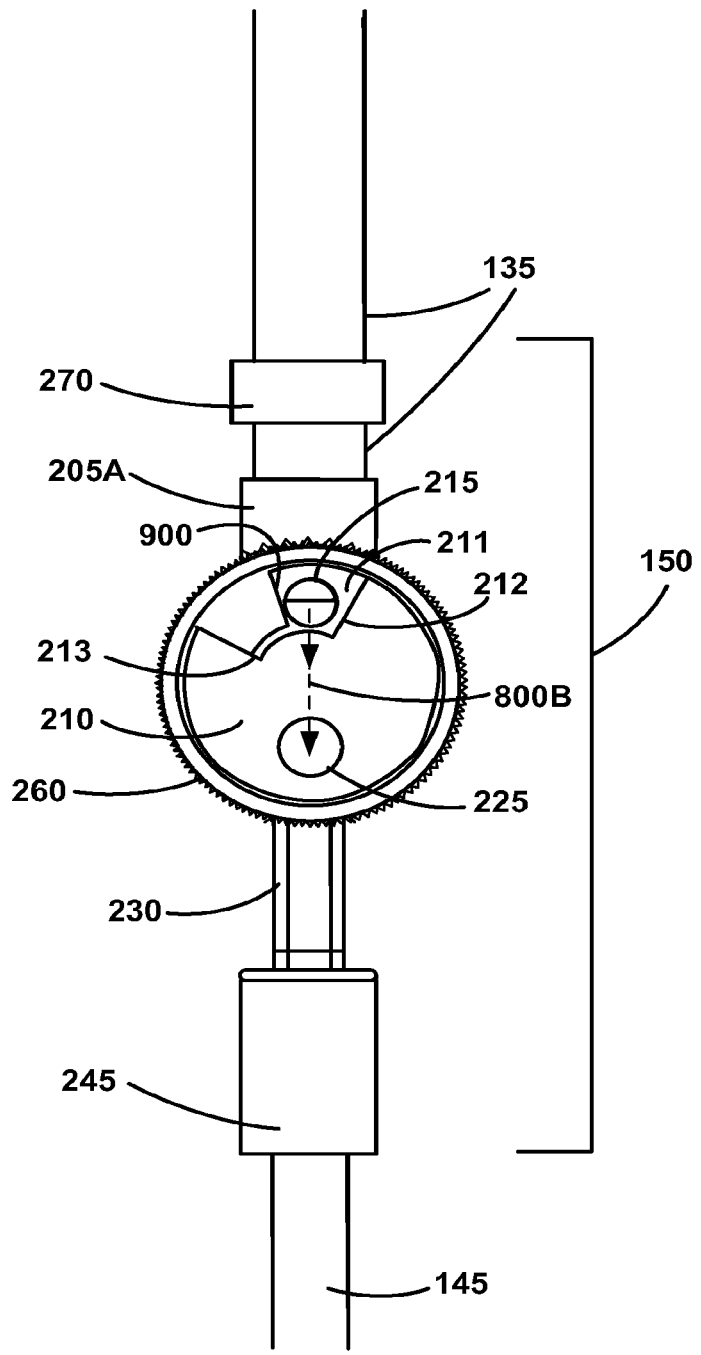
FIG. 9 is a front partial detail and sectional view of an example IV infusion tubing fitment coupled with components of an IV infusion set and showing an illustration of a fluid flow path, in accordance with an embodiment.

Body 200 defines a first inlet 205A, a first outlet 215; a second inlet 225, and a second outlet 245. Body 200 also defines an arc shaped raised flange 220 that rises out of a curved external surface 221. Flange 220 is configured for coupling with a recessed annular feature of combined pressure dome and flow control device 1000, such as in a press or snap fit. Second inlet 225 is defined in a surface 210 of body 200. Surface 210 acts as one half of a fluid flow path between first outlet 215 and second inlet 225 (with a surface of pressure dome 250 forming the other half of the fluid flow path). First outlet 215 is defined within a recessed surface 211 of body 200 (recessed with respect to surface 210). The recessing of surface 211 is configured for receiving a vane 900 (FIG. 9) of pressure dome 250, and defines a first stop 212 and a second stop 213 which limit travel of vane 900 (FIG. 9).

Body 200 may be formed of one or more pieces of injection molded biocompatible plastic (e.g., PVC, acrylic, or other suitable plastic), in one embodiment, and may be opaque or clear. In one embodiment, body 200 further includes an air-in-line (AIL) sensor fitment formed of a flexible biocompatible material. AIL sensor fitment 230 may be co-molded into body 200 and may be formed of a different material that body 200. AIL sensor fitment 230 is configured for resiliently interfacing with sensor surfaces of an AIL sensor which is included as a portion of many pumps that are utilized with IV sets. In order to resiliently interface with an AIL sensor, AIL sensor fitment 230 may be formed, in some embodiments, from silicone, thermoplastic elastomer (TPE), or some other biocompatible material which maintains resilience over a longer term.

First inlet 205A is configured for coupling with a first segment of tubing, such as pumping segment of tubing 135. By being configured for coupling, what is meant is that first inlet 205A can be coupled with a segment of tubing to create a leak free fitting, such that a fluid may flow, without leakage, from segment of tubing 135 into opening an 206A which is defined by first inlet 205A. In some embodiments, the coupling between pumping segment of tubing 135 and first inlet 205A is mechanical and does not utilize any adhesive. In some embodiments, a clamping mechanism 270 may be used to ensure a more secure, fluid tight, coupling by clamping segment of tubing 135 between clamping mechanism 270 and a portion of first inlet 205 which is disposed within tubing 135. Clamping mechanism 270 may be C-shaped as depicted, circular, or of some other well-known type.

First outlet 215 allows fluid to flow out of body 200 along a fluid flow path that leads into a pressure dome 250 (which will be described further herein). The fluid flow path flows between a surface of pressure dome 250 and surface 210 and then reenters body 200 at second inlet 225. The fluid flow path then flows through body 200 toward second inlet 225. In some embodiments, AIL sensor fitment 230 is disposed between second inlet 225 and second outlet 245 and the fluid flow path runs through AIL sensor fitment 230 before reaching second outlet 245 and exiting body 200 into tubing 145. As illustrated in Figure in some embodiments, a finger grip 240 is disposed proximate AIL sensor fitment 230 (i.e., on an opposing side of IV infusion tubing fitment 150 from AIL sensor fitment 230). The position of finger grip 240 facilitates a user grasping finger grip 240 and pushing AIL sensor fitment 230 into position between sensor elements of an AIL sensor.

Second outlet 245 is configured for coupling with a second segment of tubing, such as segment of tubing 145. By being configured for coupling, what is meant is that second outlet 245 can be coupled with a segment of tubing to create a leak free fitting, such that a fluid may flow, without leakage, from an opening 246 that is defined within second outlet 245 and into tubing 145. In some embodiments, the coupling between segment of tubing 145 and second outlet 245 is mechanical and does not utilize any adhesive, however in other embodiments, (such as when second tubing 145 is PVC tubing) an adhesive boding may be employed to facilitate coupling.

Combined pressure dome and flow control device 1000 includes knob 260 and pressure dome 250. Knob 260 may be formed of an injection molded plastic in one embodiment. Pressure dome 250 is formed of a flexible elastomeric material, in one embodiment. When IV infusion tubing fitment 150 is in an assembled state, pressure dome 250 is seated within knob 260 and knob 260 is coupled with body 200. When pressure dome 250 is seated within knob 260, surface 256 of pressure dome 250 engages with an inner surface of knob 260 to form a fluid tight seal. In this assembled state, knob 260 is rotatable and a surface 210 of body 200 and a surface of pressure dome 250 define walls of a fluid flow path between first outlet 215 and second inlet 225. Knob 260 defines a circular expansion opening 261 through which a portion of surface 255 of pressure dome 250 is able to expand in response to fluid pressure in this fluid flow path which is partially defined by a surface of pressure dome 250.

The portion of surface 255 of pressure dome 250 which expands through expansion opening 261 allows an external pressure monitor to monitor the expansion/contraction of surface 255 to monitor pressure of fluid flowing through IV infusion tubing fitment 150. For example, in one type of use of IV infusion tubing fitment 150, a pressure monitoring pin of a pumping unit or other medical device may contact surface 255 of pressure dome 250. The pin is mounted to a strain beam such that deflection of the pin by the movement of surface 255 through expansion opening 261 deflects the strain beam and creates an electrical signal which can be read by a circuit and correlated to a measurement of fluid pressure.

Figure 3:
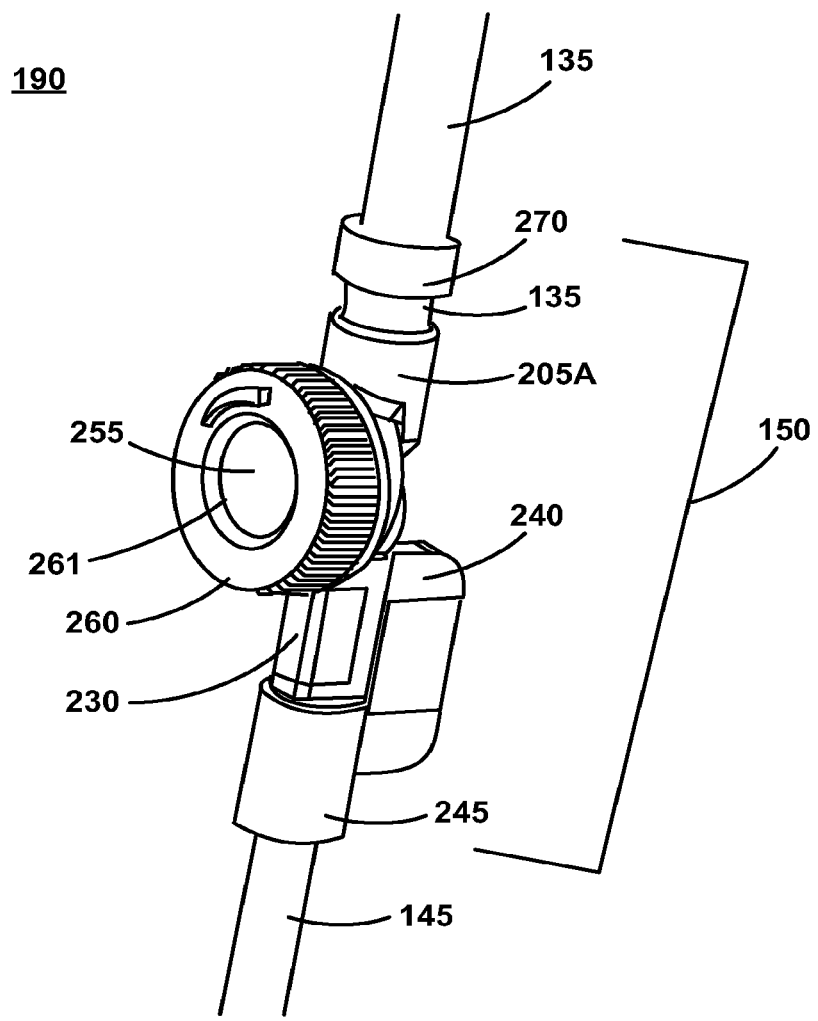
FIG. 3 is a front right detail view of an example IV infusion tubing fitment coupled with components of an IV infusion set, in accordance with an embodiment.

FIG. 3 is a front right detail view of an example IV infusion tubing fitment 150 coupled with tubing components 135, 145 of an IV infusion set, in accordance with an embodiment. FIG. 3 shows IV infusion tubing fitment 150 of FIG. 2 in an assembled state, and shows tubing 135 coupled between clamping mechanism 270 and first inlet 205A.

Figure 4:
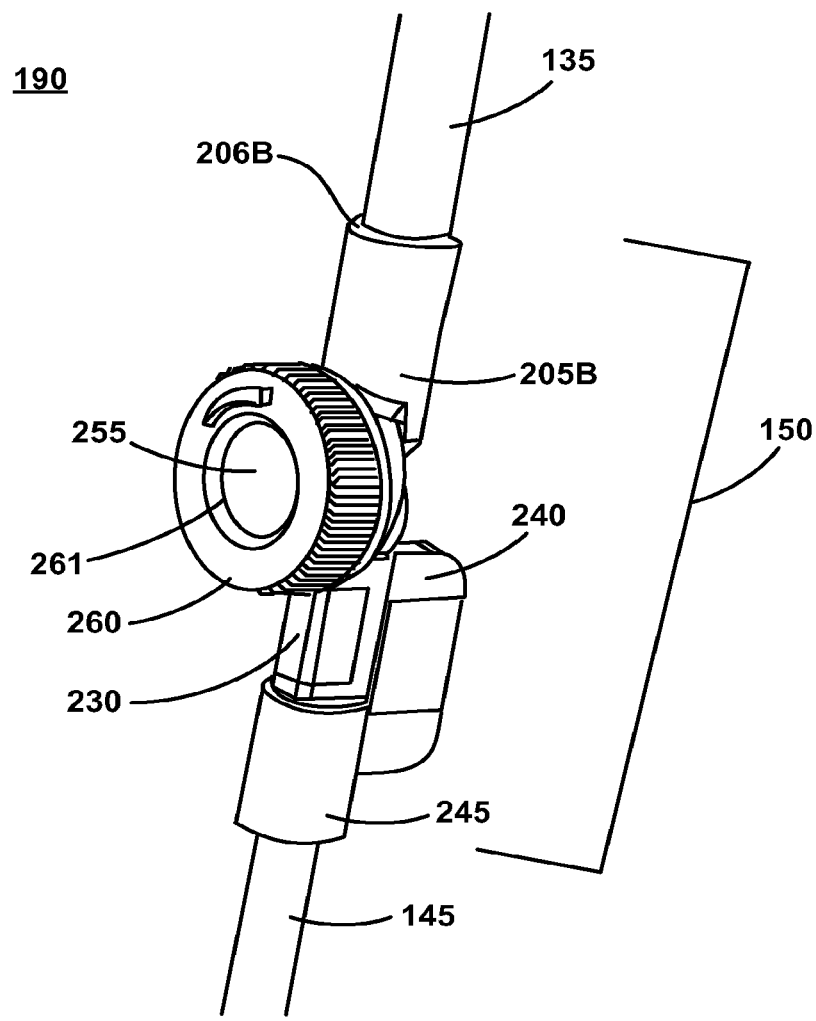
FIG. 4 is a front right detail view of an example IV infusion tubing fitment coupled with components of an IV infusion set and showing an alternative coupling to a pumping segment of tubing, in accordance with an embodiment.

FIG. 4 is a front right detail view of an example IV infusion tubing fitment 150 coupled with tubing components 135, 145 of an IV infusion set and showing an alternative coupling to a pumping segment of tubing, in accordance with an embodiment. FIG. 4 shows IV infusion tubing fitment 150 in an assembled state, and shows tubing 135 inserted within first inlet 205B as one alternative to the coupling to tubing 135 which is illustrated in FIG. 3.

Figure 5:
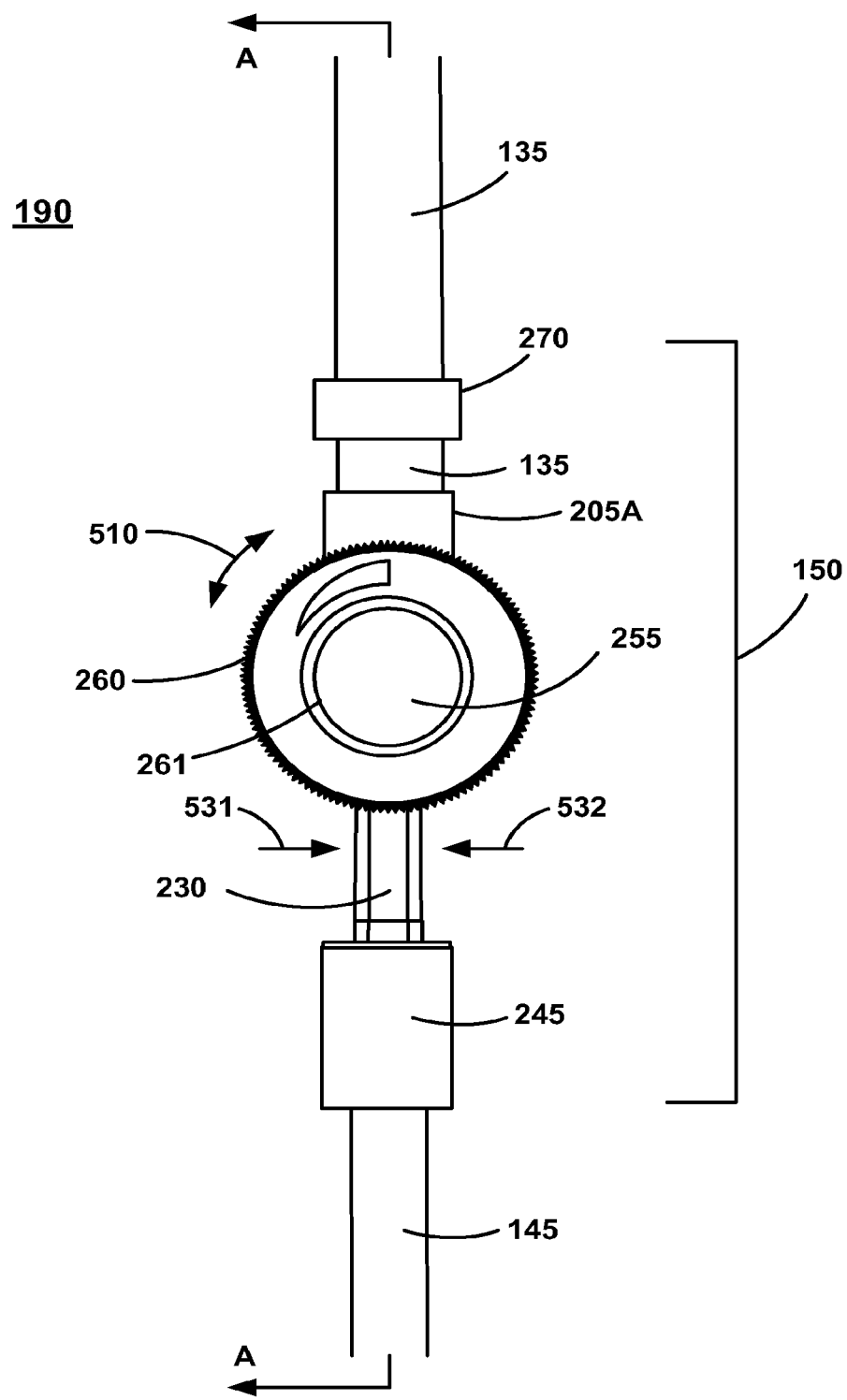
FIG. 5 is a front detail view of an example IV infusion tubing fitment coupled with components of an IV infusion set, in accordance with an embodiment.
Figure 8:
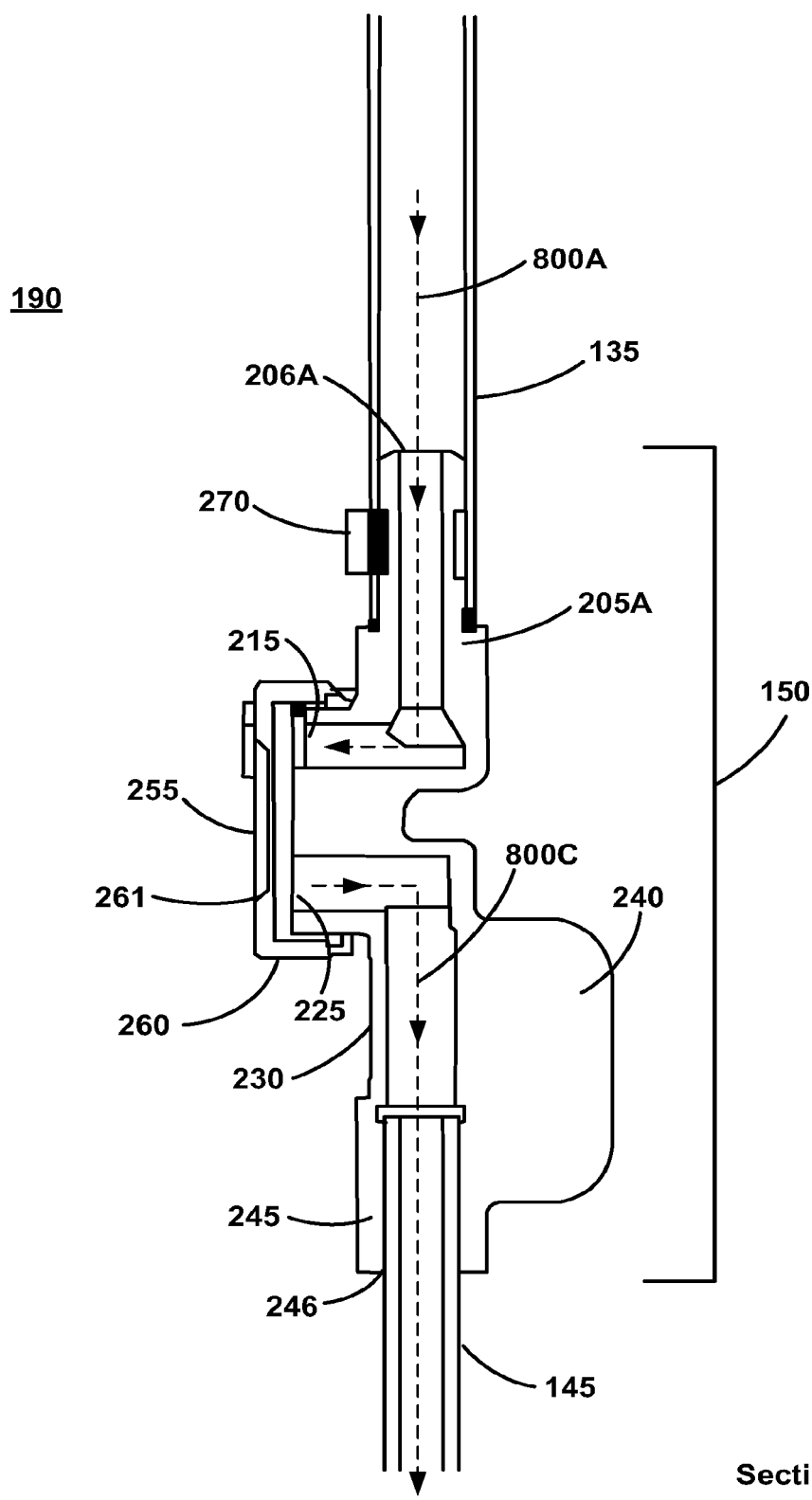
FIG. 8 is a right side detail and sectional view of an example IV infusion tubing fitment coupled with components of an IV infusion set and showing an illustration of a fluid flow path, in accordance with an embodiment.

FIG. 5 is a front detail view of an example IV infusion tubing fitment 150 coupled with tubing components 135, 145 of an IV infusion set, in accordance with an embodiment. FIG. 5 shows a front view of the IV infusion tubing fitment 150 that is illustrated in FIGS. 2 and 3. Section indicators indicate the viewing direction of Section A-A, which is illustrated in FIG. 8. Directional arrows 510 show the clockwise (CW) and counterclockwise (CCW) directions that knob 260 can be rotated. Arrows 531 and 532 show the directions which the sides of AIL sensor fitment 230 are compressed when AIL sensor fitment 230 is disposed between sensing elements of an AIL.

Many of the technologies for AIL sensing utilize an ultrasonic sensor or a light sensor. Such sensors utilize an emitter and detector disposed on opposing sides of AIL sensor fitment 230, as indicated by arrows 531 and 532. In the case of an ultrasonic sensor, the sensor emits a signal from the emitter and measures the time that the signal takes to get to the detector. A time that it takes for the ultrasonic signal to travel from the emitter to the detector can be measured. Because sound travels faster through the fluid than through air or an air-bubble, air traveling through AIL sensor fitment 230 can be sensed. With a light sensor, a difference in time may be measured and/or a disruption (caused by air-in-line) may be measured.

In order to get those types of AIL sensors to operate properly and reliably, a good coupling between the AIL sensor's elements and a portion of an IV infusion set is required. Usually there is a "pocket" of some sort that a tubing or some portion of the IV infusion set is pushed into so that it will be wedged between the elements of the AIL sensor, which are on the sides of the pocket. When PVC tubing is initially compressed, it resists the compression with a rebounding force that tries to maintain its original shape. However, overtime, this rebounding force diminishes or relaxes and the PVC tubing assumes the shape it was forced into and pulls away from the walls of the pocket where the sensor elements are located. This is referred to as stress relaxation, and becomes an issue with PVC tubing when it "relaxes" under stress with time pulling away from the elements of the AIL sensor, leading to faulty readings, false AIL alarms, and poor functioning of the AIL sensor.

In order to get a better coupling that lasts for a longer period of time, in some embodiments, AIL sensor fitment 230 is made of silicone, thermoplastic elastomer (TPE), or some other biocompatible material which maintains resilience over a longer term than PVC tubing (i.e., does not have the stress relaxation issues of PVC tubing). Additionally, in some embodiments, AIL sensor fitment 230 is shaped with flat sides (rather than rounded) such that it gives more contact to the sides of an AIL sensor pocket where the sensor elements are located than rounded surfaces of a round tubing would give. This allows AIL sensor fitment 230 to maintain resilient pressure against AIL sensor faces much longer than PVC tubing.

Figure 6:
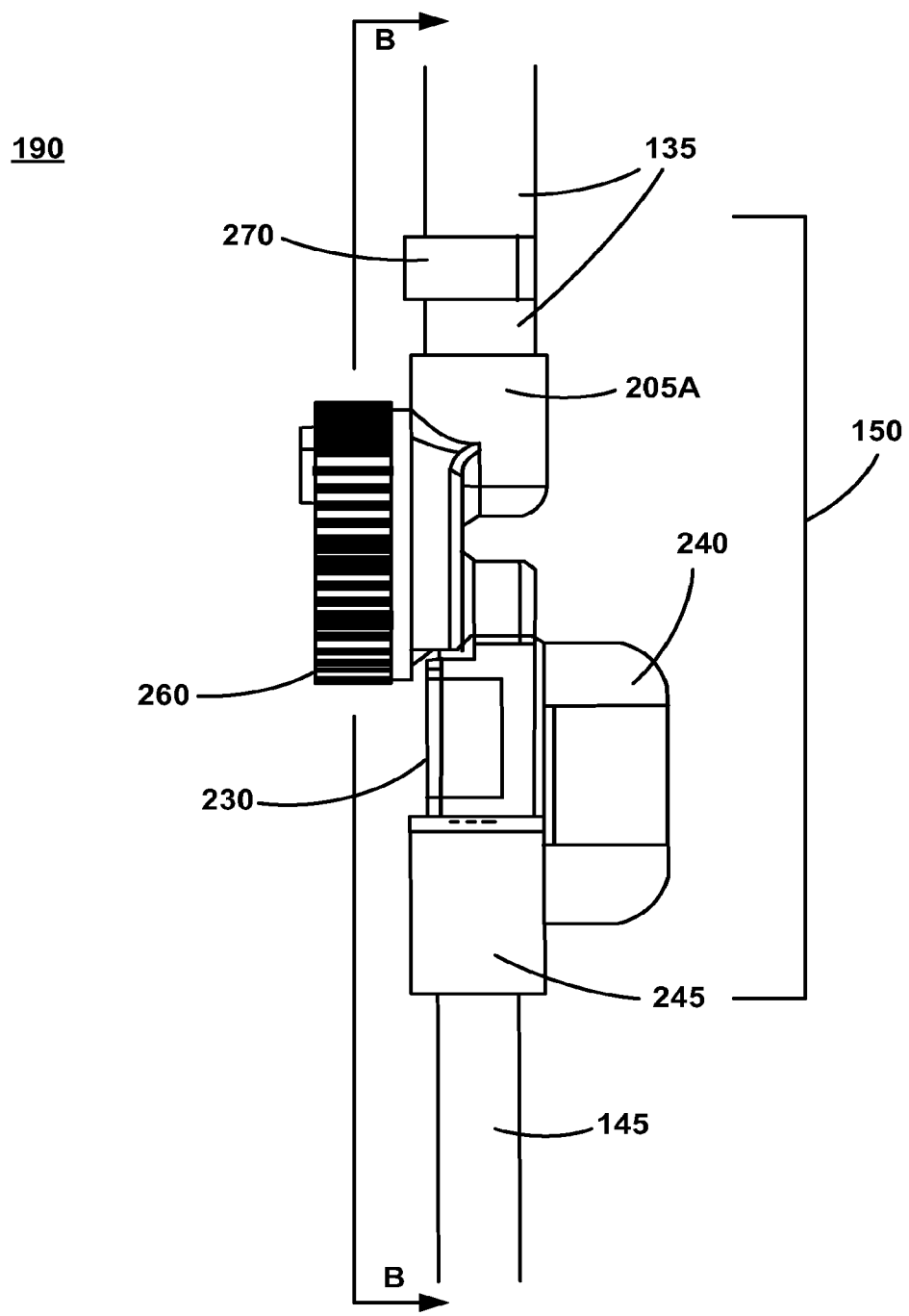
FIG. 6 is a right side detail view of an example IV infusion tubing fitment coupled with components of an IV infusion set, in accordance with an embodiment.

FIG. 6 is a right side detail view of an example IV infusion tubing fitment 150 coupled with tubing components 135, 145 of an IV infusion set, in accordance with an embodiment. FIG. 6 shows a right side view of the IV infusion tubing fitment 150 that is illustrated in FIGS. 2, 3, and 5. Section indicators indicate the viewing direction of partial Section B - B, which is illustrated in FIG. 9. It is appreciated that a similar view from the left side is substantially symmetrical.

Figure 7A:
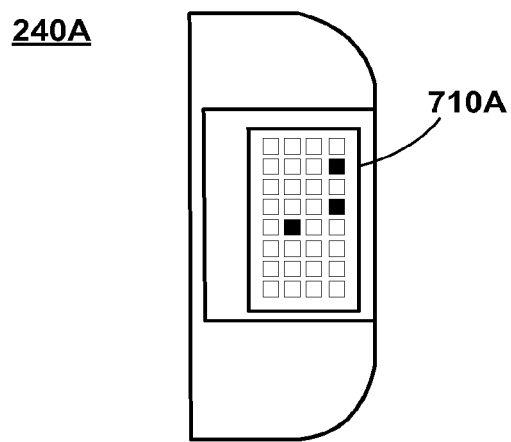
FIGS. 7A and 7B are right side detail views of finger grips, in accordance with various embodiments.
Figure 7B:
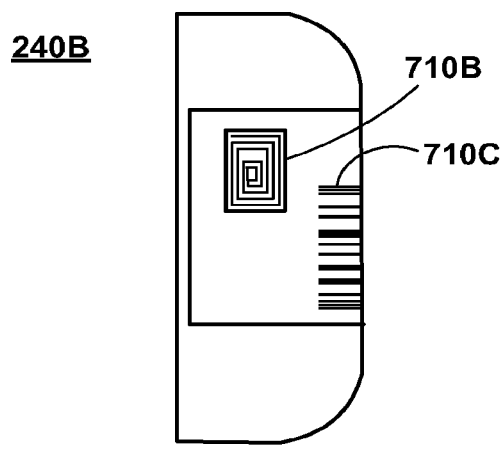

FIGS. 7A and 7B are right side detail views of finger grips, in accordance with various embodiments. In one embodiment, in addition to providing finger gripping surfaces, finger grip 240 provides a surface upon which an identification mechanism 710 may be disposed. Identification mechanism 710 may be one of many identification mechanisms which can provide a unique identification associated with IV infusion tubing fitment 150 and/or set 100 in response to an interrogation. For example, as illustrated in FIG. 7A, in one embodiment, identification mechanism 710A is a plurality of optical windows, some of which are optically clear and some of which are covered or occluded such that when interrogated by a light emitting and detecting sensor the plurality of windows form a code or identifier. As illustrated in FIG. 7B, one or more of a radio frequency identification (RFID) tag 710B and a bar code 710C may also be disposed upon finger grip 240. It is appreciated that one or more of these or other identification mechanisms 710 may be employed independently or in combination. In one embodiment, such a unique identifier of an identification mechanism 710 can be used for auditing stock, or otherwise keeping track of IV infusion tubing fitment(s) 150 or IV infusion set(s) 100 in which IV infusion tubing fitment 150 is included.

In one embodiment, identification mechanism 710 is configured to be interrogated by and to provide its unique identifier to an interrogator that is coupled with a pump, AIL sensor, or other medical device with which IV infusion set 100 is utilized. That is, identification mechanism 710 is located such that it is easily interrogated by such a pump, AIL sensor, or other medical device with which it is utilized. In this manner, IV infusion set 100 can be uniquely identified and a start use time can be established. The pump, AIL sensor, or other medical device, can then sound an alarm when a specified time of use has elapsed and the IV infusion set 100 is required to be replaced or evaluated. Likewise, the pump, AIL sensor, or other medical device can discern when a replacement has occurred as a newly installed IV infusion set 100 will include an IV infusion tubing fitment 150 that responds, when interrogated, with a different unique identifier than the replaced item. In addition, multiple types of IV infusion sets are available that are used for specific medical treatments, for example low absorbing configurations compatible with chemotherapy, nitroglycerin and TPN (total parenteral nutrition) therapies. The pump can sound an alarm if an incorrect IV infusion set 100 is used for the treatment being administered.

FIG. 8 is a right side detail and sectional view A-A of an example 1V infusion tubing fitment 150 coupled with tubing components 135, 145 of an IV infusion set and showing an illustration of a fluid flow path 800, in accordance with an embodiment. In FIG. 8, two of three portions (800A and 800C) of fluid flow path 800 are illustrated. Fluid flow path 800A enters opening 206A which is defined by first inlet 205A, and flows through first inlet 205A into body 200, toward first outlet 215, and out of body 200 via first outlet 215. Fluid flow path 800C enters second inlet 225 and again flows through body 200, which includes flowing through AIL sensor fitment 230, and out of body 200 via opening 246 which is defined by second outlet 245.

FIG. 9 is a front partial detail and sectional view B-B of an example IV infusion tubing fitment 150 coupled with tubing components 135, 145 of an IV infusion set and showing an illustration of a fluid flow path, in accordance with an embodiment. In FIG. 9, the third portion (800B) of fluid flow path 800 is illustrated. Fluid flow path 800B exits from body 200 via first outlet 215, and flows into a space between surface 212 and an inner surface 1055 (FIGS. 10C and 10D) of pressure dome 250, fluid flow path 800B then exits this space and reenters body 200 via second inlet 225.

The partial sectioning has removed the outer surfaces of knob 260 and pressure dome 250, but has left vane 900 visible. As is more apparent from FIGS. 10C and 10D, vane 900 is coupled with, co-molded with, or formed as a contiguous portion of pressure dome 250. Because pressure dome 250 is coupled with knob 260, vane 900 can be rotated between stop 212 and stop 213 in response to rotation of knob 260 in CW and CCW directions about flange 220.

As depicted in FIG. 9, knob 260 has been rotated CCW about flange 220 until vane 900 has engaged stop 213. In this position, first outlet 215 is fully open and fluid flow path 800B is unrestricted by vane 900. By rotating knob 260 in a CW direction about flange 220, vane 900 will move along recessed surface 211 and will variably regulate the flow of fluid through fluid flow path 800B by gradually closing off first outlet 215 until it is fully blocked by vane 900. With further CW rotation, shortly after fully blocking first outlet 215, vane 900 will engage stop 212 and will be prevented from further rotation. When vane 900 is engaged with stop 212, first outlet 215 and fluid flow path 800B are fully blocked by vane 900. The flow on fluid flow path may be variably increased then by rotating knob 260 (and thus vane 900) in a CCW direction to variably unblock first outlet 215. Although depicted as requiring CCW rotation to variably unblock/open first outlet 215 and CW rotation to variably block/close first outlet 215, it is appreciated that recessed surface 211 and stops 212 and 213 could easily be positioned such that these directions of rotation are reversed.

Figure 10A:
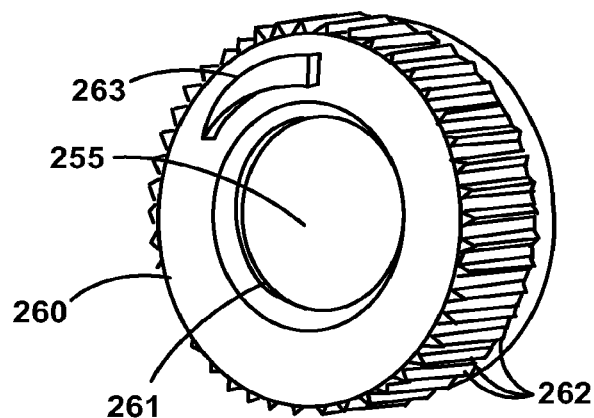
FIG. 10A is a right front view of a combined pressure dome and flow control device, in accordance with an embodiment.

FIG. 10A is a right front view of a combined pressure dome and flow control device 1000, in accordance with an embodiment. FIG. 10A illustrates an assembled state of combined pressure dome and flow control device 1000. As depicted, pressure dome 250 (FIG. 10B) is directly seated in contact within knob 260 such that surface 255 of pressure dome 250 interfaces with the circular edges of knob 260 which define opening 261. As can be seen in FIG. 10A, the outer circumference of knob 260 may include teeth 262 or other grip enhancing features disposed thereon. Such teeth 262 or other grip enhancing features may be molded into knob 260. A flow control symbol 263 and/or other indicia may be disposed upon a surface of knob 260 either as an indented or as a raised feature. Flow control symbol 263 or other indicia may be molded into knob 260.

Figure 10B:
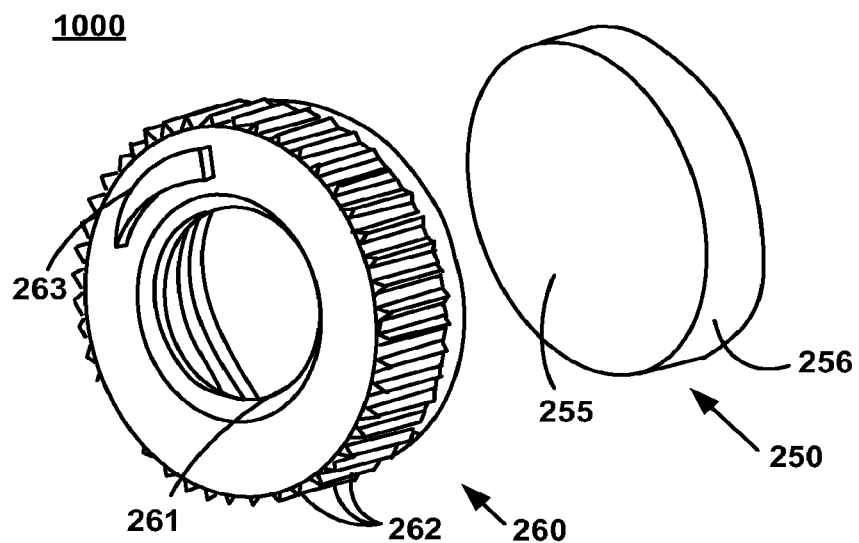
FIG. 10B is a right front exploded view of a combined pressure dome and flow control device, in accordance with an embodiment.

FIG. 10B is a right front exploded view of a combined pressure dome and flow control device 1000, in accordance with an embodiment. FIG. 10B is an enlargement of the view of combined pressure dome and flow control device 1000 that is illustrated in FIG. 2.

Figure 10C:
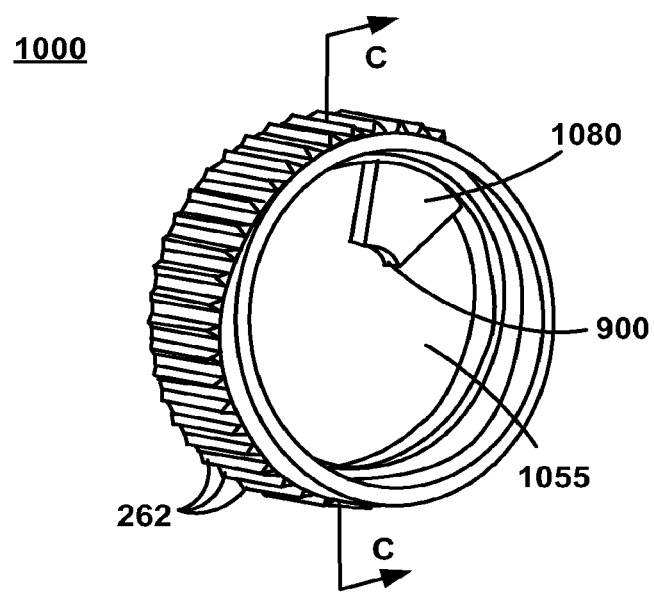
FIG. 10C is a right rear view of a combined pressure dome and flow control device, in accordance with an embodiment.

FIG. 10C is a right rear view of a combined pressure dome and flow control device 1000, in accordance with an embodiment. In one embodiment, FIG. 10C is a rear view of FIG. 10A. FIG. 10C illustrates an assembled state of combined pressure dome and flow control device 1000. As depicted, pressure dome 250 is seated within knob 260. Vane 900 is visible. In various embodiments, Vane 900 is coupled with, co-molded as a part of, or formed as a continuous portion of pressure dome 250. Surface 1080 of vane 900 interfaces with recessed surface 211 of body 200 when body 200 and combined pressure dome and flow control device 1000 are in an assembled state (see e.g., FIGS. 3, 5, and 6 for representations of such an assembled state). In this same assembled state, surface 1055 and surface 211 form the inner and outer walls of fluid flow path 800B (see FIG. 9). Fluid pressure against surface 1055 (from fluid flowing on fluid flow path 800B) causes surface 255 of pressure dome 250 to variably expand outward through opening 261 in accordance with the pressure. Section arrows indicated the direction of view of a Section C-C, which is illustrated in FIG. 11.

Figure 10D:
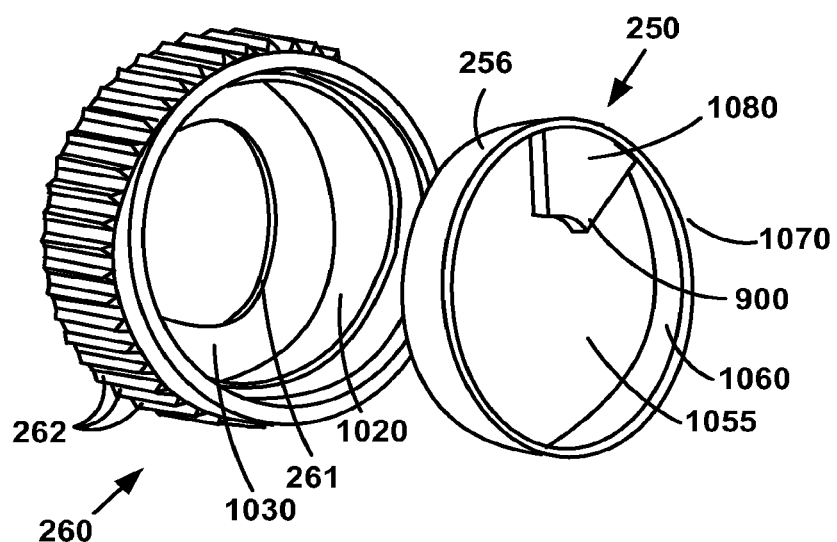
FIG. 10D is a right rear exploded view of a combined pressure dome and flow control device, in accordance with an embodiment.

FIG. 10D is a right rear exploded view of a combined pressure dome and flow control device 1000, in accordance with an embodiment. FIG. 10D illustrates surface 1020 of knob 260 against which surface 256 is seated and surface 1030 against which a portion of surface 255 is seated, when combined pressure dome and flow control device 1000 is assembled as shown in FIGS. 10A and 10C. When combined pressure dome and flow control device 1000 and body 200 are assembled into IV infusion tubing fitment 150, surface 1060 interfaces with curved external surface 221 (FIG. 2) of body 200 and surface 1070 interfaces with flange 220 to provide a fluid tight seal.

Figure 11:
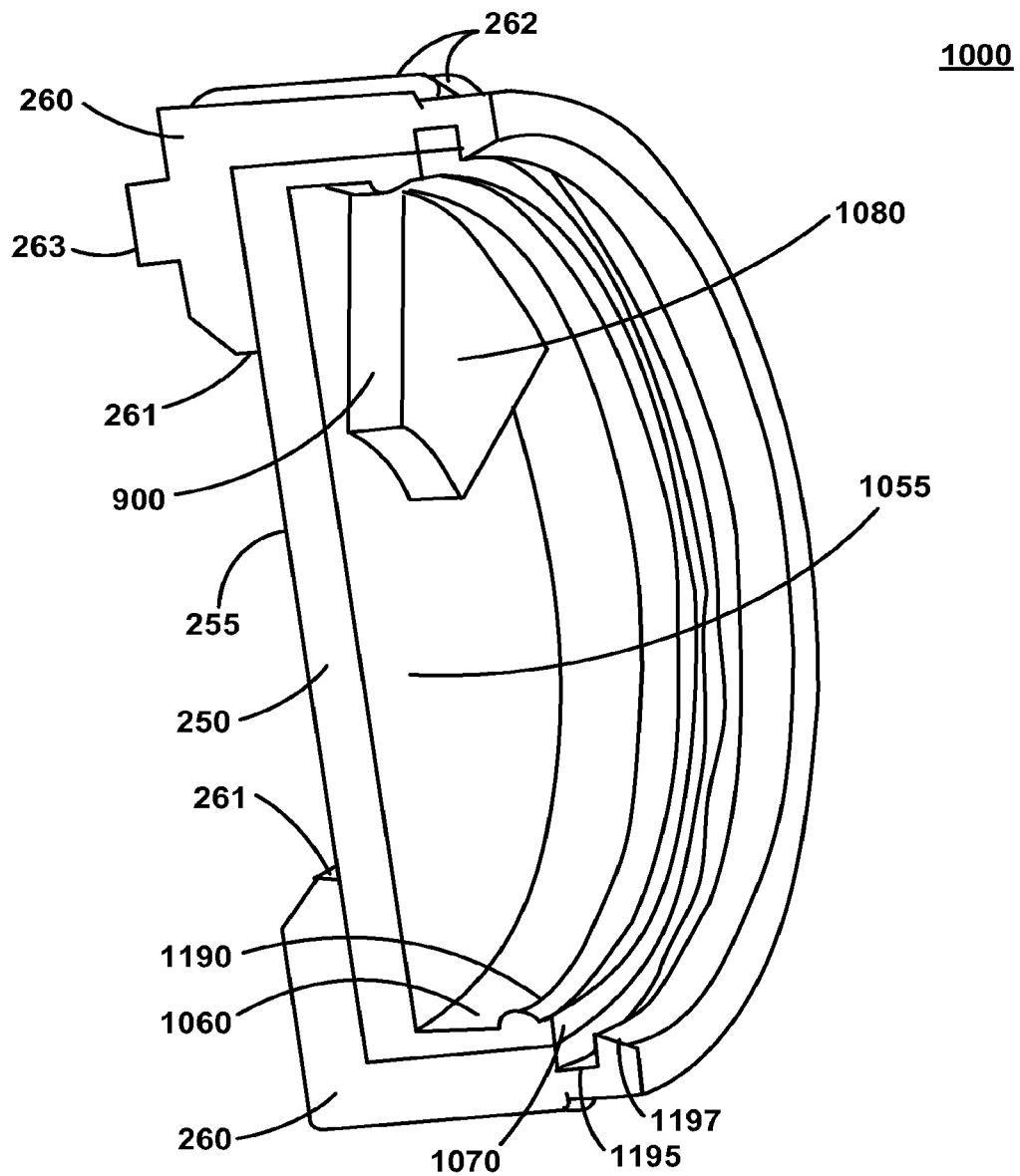
FIG. 11 is a right rear sectional view of a combined pressure dome and flow control device, in accordance with an embodiment.

FIG. 11 is a right rear sectional view C-C of a combined pressure dome and flow control device 1000, in accordance with an embodiment. FIG. 11 illustrates an annular recess 1195 which is formed in inner surface 1020 of knob 260. When combined pressure dome and flow control device 1000 and body 200 are assembled into IV infusion tubing fitment 150, flange 220 of body 200 becomes seated within recess 1195. In one embodiment, such assembly through a press or snap fit is facilitated by angled portion 1197 of knob 260, which acts as a ramp when pressed against flange 220. In some embodiments, pressure dome 250 further includes a raised annular lip 1190, which further facilitates a fluid tight seal between combined pressure dome and flow control device 1000 and surface 221 of body 200.

The foregoing descriptions of specific embodiments have been presented for purposes of illustration and description. They are not intended to be exhaustive or to limit the presented technology to the precise forms disclosed, and obviously many modifications and variations are possible in light of the above teaching. The figures and embodiments were chosen and described in order to best explain the principles of the presented technology and its practical application, to thereby enable others skilled in the art to best utilize the presented technology and various embodiments with various modifications as are suited to the particular use contemplated.

What is claimed is:

1. An intravenous infusion tubing fitment, the tubing fitment comprising:
   a body which defines:
   a first inlet configured for coupling with a first segment of tubing;
   a first outlet into a pressure dome;
   a second inlet from the pressure dome;
   a second outlet configured for coupling with a second segment of tubing; and
   an air-in-line (AIL) sensor fitment configured for resiliently interfacing with sensor surfaces of an air-in-line sensor;
   a rotatable knob coupled with the body, wherein the knob defines an expansion opening within a surface of the knob; and
   the pressure dome formed of a flexible elastomeric material, the pressure dome seated directly within the knob in contact with the knob to define a fluid flow path between the first outlet and the second inlet, the pressure dome configured to expand through the expansion opening in response to fluid pressure in the fluid flow path.

2. The tubing fitment of claim 1, wherein the air-in-line (AIL) sensor fitment is formed of a flexible biocompatible material and co-molded into the body.

3. The tubing fitment of claim 1, wherein the body further comprises a finger grip disposed proximate the AIL sensor fitment.

4. The tubing fitment of claim 3, wherein the finger grip comprises an identification mechanism configured to provide a unique identification associated with the intravenous infusion tubing fitment.

5. The tubing fitment of claim 4, wherein the identification mechanism comprises a plurality of optical windows, wherein some of the optical windows are optically clear and some covered or occluded.

6. The tubing fitment of claim 4, wherein the identification mechanism comprises one or more of a radio frequency identification (RFID) tag and a bar code disposed upon the finger grip.

7. The tubing fitment of claim 1, wherein the AIL sensor fitment comprises silicone, thermoplastic elastomer (TPE), or a biocompatible material that maintains resilience.

8. The tubing fitment of claim 1, further comprising:
   an identification mechanism configured for uniquely identifying the tubing fitment in response to an interrogation.

9. The tubing fitment of claim 1, wherein the pressure dome comprises a vane configured to variably regulate flow through the fluid flow path in response to rotation of the knob.

10. The tubing fitment of claim 9, wherein the body further comprises: a recessed portion configured to receive the vane.

11. The tubing fitment of claim 10, wherein the body further comprises:
    a first stop defined in the recessed portion and configured for limiting travel of the vane and the knob in a first direction such that the vane fully blocks the first outlet when engaged with the first stop; and
    a second stop defined in the recessed portion and configured for limiting travel of the vane and the knob in a second direction such that the vane blocks no portion of the first outlet when engaged with the second stop.

12. The tubing fitment of claim 1, wherein the expansion opening extends entirely through the knob such that the pressure dome is exposed through the expansion opening when the pressure dome is seated in the knob.

13. The tubing fitment of claim 1, wherein the pressure dome has an annular wall that defines a cavity and further comprising a vane extending radially inward from the annular wall into the cavity of the pressure dome toward an axis of rotation of the knob, wherein the vane is configured to variably regulate flow through the fluid flow path in response to rotation of the knob as it moves between a first position wherein the vane fully blocks fluid flow through the fluid flow path and a second position wherein the vane does not block fluid flow through the fluid flow path.

14. An intravenous infusion tubing fitment, the tubing fitment comprising:
    a body comprising:
    a first inlet configured for coupling with a first segment of tubing and forming an entrance of a fluid flow path through the tubing fitment;
    a first outlet configured for coupling the fluid flow path from the body into a combined pressure dome and flow control device;
    a flange configured for coupling with the combined pressure dome and flow control device; a second inlet configured for coupling the fluid flow path from the combined pressure dome and flow control device back into the body;
    a second outlet configured for coupling with a second segment of tubing and providing an exit of the fluid flow path from the tubing fitment;
    an air-in-line (AIL) sensor fitment formed of a flexible biocompatible material and co-molded into the body as a portion of the fluid flow path, the AIL sensor fitment configured for resiliently interfacing with sensor surfaces of an AIL sensor; and
    a finger grip disposed proximate the AIL sensor fitment; and
    a combined pressure dome and flow control device comprising:
    a knob which defines an expansion opening and further defines a recessed annular feature configured for coupling with the flange;
    a pressure dome formed of a flexible elastomeric material and being seated directly within the knob in contact with the knob to define the fluid flow path between the first outlet and the second inlet, and the pressure dome configured to expand through the expansion opening in response to fluid pressure in the fluid flow path.

15. The tubing fitment of claim 14, wherein the finger grip includes an identification mechanism configured for uniquely identifying the tubing fitment in response to an interrogation.

16. The tubing fitment of claim 15, wherein in the identification mechanism comprises a plurality of optical windows.

17. The tubing fitment of claim 15, wherein the identification mechanism comprises a radio frequency identification (RFID) tag.

18. The tubing fitment of claim 15, wherein the body further comprises a vane configured to regulate flow of fluid through the fluid flow path in response to rotation of the knob.

19. The tubing fitment of claim 14, wherein the expansion opening extends entirely through the knob such that the pressure dome is exposed through the expansion opening when the pressure dome is seated in the knob.

20. The tubing fitment of claim 14, wherein the pressure dome has an annular wall that defines a cavity and further comprising a vane extending radially inward from the annular wall into the cavity of the pressure dome toward an axis of rotation of the knob, wherein the vane is configured to variably regulate flow through the fluid flow path in response to rotation of the knob as it moves between a first position wherein the vane fully blocks fluid flow through the fluid flow path and a second position wherein the vane does not block fluid flow through the fluid flow path.

21. A method comprising:
assembling an intravenous infusion tubing fitment, the tubing fitment comprising:
a body comprising:
a first inlet configured for coupling with a first segment of tubing and forming an entrance of a fluid flow path through the tubing fitment;
a first outlet configured for coupling the fluid flow path from the body into a combined pressure dome and flow control device;
a flange configured for coupling with the combined pressure dome and flow control device;
a second inlet configured for coupling the fluid flow path from the combined pressure dome and flow control device back into the body;
a second outlet configured for coupling with a second segment of tubing and providing an exit of the fluid flow path from the tubing fitment; and
a combined pressure dome and flow control device comprising:
a knob which defines an expansion opening and further defines a recessed annular feature configured for coupling with the flange;
a pressure dome formed of a flexible elastomeric material and configured for being seated directly within the knob in contact with the knob to define the fluid flow path between the first outlet and the second inlet, and the pressure dome configured to expand through the expansion opening in response to fluid pressure in the fluid flow path.

22. The method of claim 21, wherein the body further comprises an air-in-line (AIL) sensor fitment formed of a flexible biocompatible material and co-molded into the body as a portion of the fluid flow path, the AIL sensor fitment configured for resiliently interfacing with sensor surfaces of an AIL sensor.

23. The method of claim 22, wherein the body further comprises a finger grip disposed proximate the AIL sensor fitment.

24. The method of claim 23, wherein the finger grip further comprises an identification mechanism configured for uniquely identifying the tubing fitment in response to an interrogation.

25. The method of claim 21, wherein the expansion opening extends entirely through the knob such that the pressure dome is exposed through the expansion opening when the pressure dome is seated in the knob.

26. The method of claim 21, wherein the pressure dome has an annular wall that defines a cavity and further comprising a vane extending radially inward from the annular wall into the cavity of the pressure dome toward an axis of rotation of the knob, wherein the vane is configured to variably regulate flow through the fluid flow path in response to rotation of the knob as it moves between a first position wherein the vane fully blocks fluid flow through the fluid flow path and a second position wherein the vane does not block fluid flow through the fluid flow path.

* * * * *